(12) United States Patent
Pestes

(10) Patent No.: US 10,232,245 B2
(45) Date of Patent: Mar. 19, 2019

(54) WHEELCHAIR EXERCISE APPARATUS HAVING INDEPENDENT DRIVE ROLLERS

(71) Applicant: Wheelers' Paramill, LLC, Sandy, OR (US)

(72) Inventor: Larry Pestes, Boring, OR (US)

(73) Assignee: WHEELERS' PARAMILL INC., Boring, OR (US)

( * ) Notice: Subject to any disclaimer, the term of this patent is extended or adjusted under 35 U.S.C. 154(b) by 5 days.

(21) Appl. No.: 15/713,182

(22) Filed: Sep. 22, 2017

(65) Prior Publication Data

US 2018/0071609 A1 Mar. 15, 2018

Related U.S. Application Data

(63) Continuation-in-part of application No. 14/573,884, filed on Dec. 17, 2014, now abandoned.

(51) Int. Cl.
| | |
|---|---|
| *A63B 71/06* | (2006.01) |
| *A63B 22/00* | (2006.01) |
| *A63B 24/00* | (2006.01) |
| *A63B 71/00* | (2006.01) |
| *A63B 21/00* | (2006.01) |
| *G06F 19/00* | (2018.01) |
| *G01C 22/00* | (2006.01) |
| *A63B 21/005* | (2006.01) |
| *A63B 23/035* | (2006.01) |
| *A63B 23/12* | (2006.01) |
| *A61G 5/10* | (2006.01) |
| *A63B 21/008* | (2006.01) |
| *A63B 21/015* | (2006.01) |

(Continued)

(52) U.S. Cl.
CPC ...... *A63B 71/0619* (2013.01); *A63B 21/0056* (2013.01); *A63B 21/4049* (2015.10); *A63B 23/03541* (2013.01); *A63B 23/1209* (2013.01); *A63B 24/0003* (2013.01); *A63B 24/0062* (2013.01); *A63B 71/0009* (2013.01); *G01C 22/006* (2013.01); *G06F 19/3481* (2013.01); *A61G 5/10* (2013.01); *A63B 21/00069* (2013.01); *A63B 21/0083* (2013.01); *A63B 21/0088* (2013.01); *A63B 21/015* (2013.01); *A63B 21/151* (2013.01); *A63B 21/158* (2013.01); *A63B 21/225* (2013.01); *A63B 23/1263* (2013.01); *A63B 24/0087* (2013.01); *A63B 71/0622* (2013.01); *A63B 2024/0071* (2013.01); *A63B 2069/161* (2013.01); *A63B 2069/168* (2013.01); *A63B 2071/0018* (2013.01); *A63B 2071/065* (2013.01); *A63B 2071/0641* (2013.01); *A63B 2071/0652* (2013.01); *A63B 2220/34* (2013.01); *A63B 2225/02* (2013.01); *A63B 2225/09* (2013.01)

(58) Field of Classification Search
CPC combination set(s) only.
See application file for complete search history.

(56) References Cited

U.S. PATENT DOCUMENTS

| 1,525,278 A | 2/1925 | Doglione |
| 2,709,362 A | 5/1955 | Marcus et al. |

(Continued)

FOREIGN PATENT DOCUMENTS

JP 11332917 A 12/1999

*Primary Examiner* — Joshua Lee
*Assistant Examiner* — Shila Jalalzadeh Abyaneh
(74) *Attorney, Agent, or Firm* — Workman Nydegger

(57) ABSTRACT

An exercise apparatus for a wheelchair.

5 Claims, 8 Drawing Sheets

(51) Int. Cl.
  *A63B 21/22*   (2006.01)
  *A63B 69/16*   (2006.01)

(56) References Cited

U.S. PATENT DOCUMENTS

| | | |
|---|---|---|
| 2,788,211 A | 4/1957 | Ivanoff |
| 3,125,341 A | 3/1964 | Carrington |
| 3,423,086 A | 1/1969 | Moore |
| 4,233,844 A | 11/1980 | Dreisinger et al. |
| 4,911,425 A | 3/1990 | Kynast et al. |
| 4,938,474 A | 7/1990 | Sweeney et al. |
| 4,966,362 A | 10/1990 | Ramaekers |
| 5,076,792 A | 12/1991 | Niermann |
| 5,230,418 A | 7/1993 | Agnoff |
| 5,277,685 A | 1/1994 | Gonzales |
| 5,476,429 A * | 12/1995 | Bigelow ............ A63B 21/0056 414/921 |
| 5,643,143 A | 7/1997 | Burak et al. |
| 5,649,883 A | 7/1997 | Mayes et al. |
| 5,704,876 A | 1/1998 | Baatz |
| 5,709,631 A | 1/1998 | Kleinsasser |
| 6,113,519 A | 9/2000 | Goto |
| 6,645,127 B1 | 11/2003 | Pestes |
| 6,716,143 B1 | 4/2004 | Martin |
| 7,004,885 B1 | 2/2006 | Wu et al. |
| 7,604,572 B2 | 10/2009 | Stanford |
| 7,874,962 B1 | 1/2011 | Pestes |
| 2006/0276306 A1 | 12/2006 | Pan et al. |
| 2007/0049470 A1 * | 3/2007 | Pyles .................. A63B 21/068 482/95 |

* cited by examiner

WHEELCHAIR EXERCISE APPARATUS HAVING INDEPENDENT DRIVE ROLLERS

CROSS REFERENCE TO RELATED APPLICATIONS

The present application is a continuation-in-part of application Ser. No. 14/573,884 filed on Dec. 17, 2014.

BACKGROUND OF THE INVENTION

Exercise apparatuses for use by people in wheelchairs are well known. These apparatuses typically operate by supporting the driving wheels of the wheelchair on a roller which is connected to a flywheel. A brake is provided on the flywheel to allow a variable amount of resistance to be asserted against the driving wheels. However, these prior art apparatuses are not capable of informing the user if more force is being applied to one of the driving wheels than is being applied to the other, and do not allow a different amount of resistance to be applied to each driving wheel. The prior art apparatuses also do not allow the user to rotate each driving wheel at a different speed to simulate turning the wheelchair. In addition, the prior art apparatuses are configured for use with a traditional wheelchair, having two large side-by-side driving wheels located at or slightly behind the seat and two smaller side-by-side rotatable wheels located at or slightly forward of the seat. Thus, they do not work for sports or racing wheelchairs of the type having a single front wheel which is located further forward of the driving wheels than in a conventional wheelchair and is centered between the driving wheels.

BRIEF DESCRIPTION OF THE SEVERAL DRAWINGS

Figure 9A:
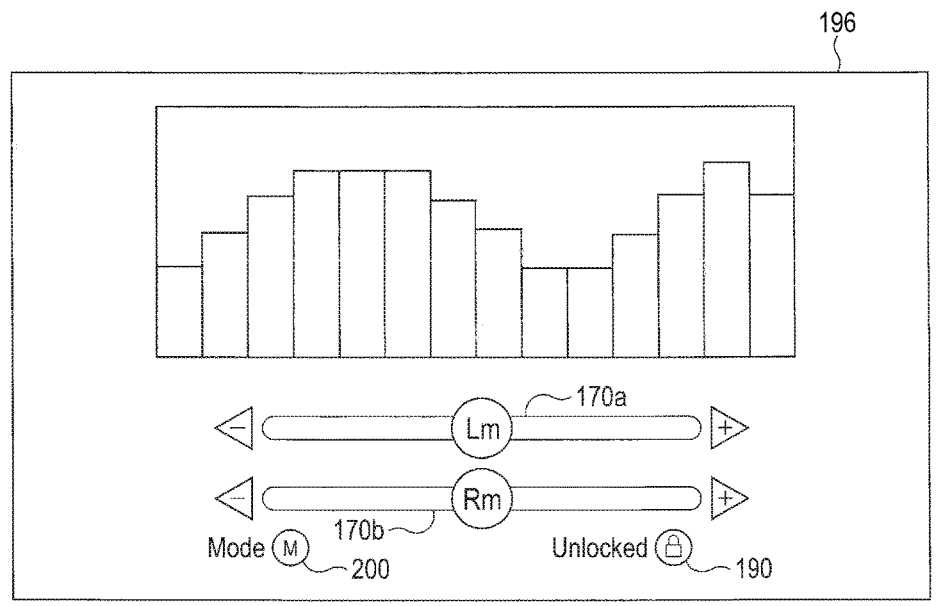
Figure 9B:
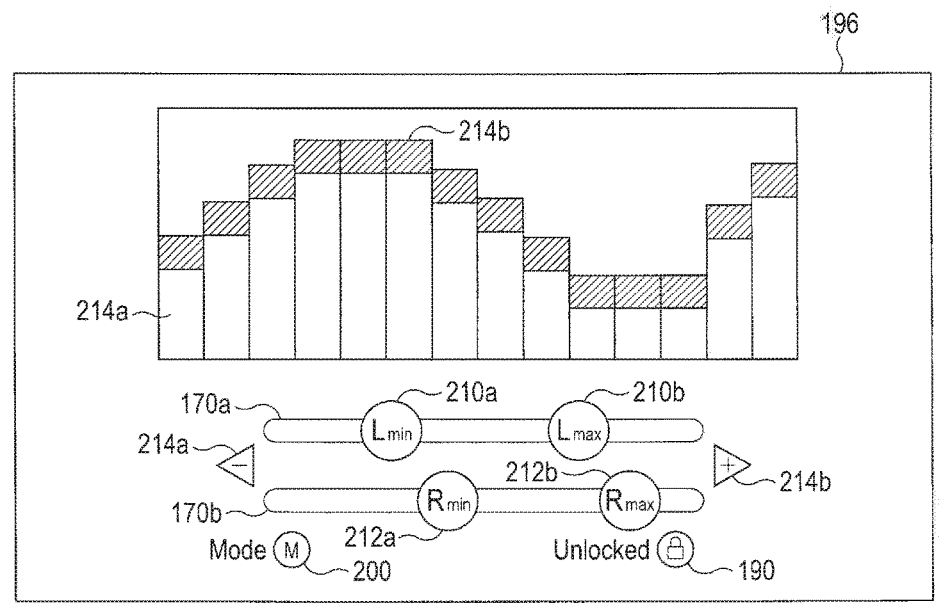

FIGS. 9A and 9B each show further alternate embodiments of a control system for independently setting the respective resistances of brakes of a wheelchair exercise apparatus.

DETAILED DESCRIPTION OF PREFERRED EMBODIMENTS

Figure 1:
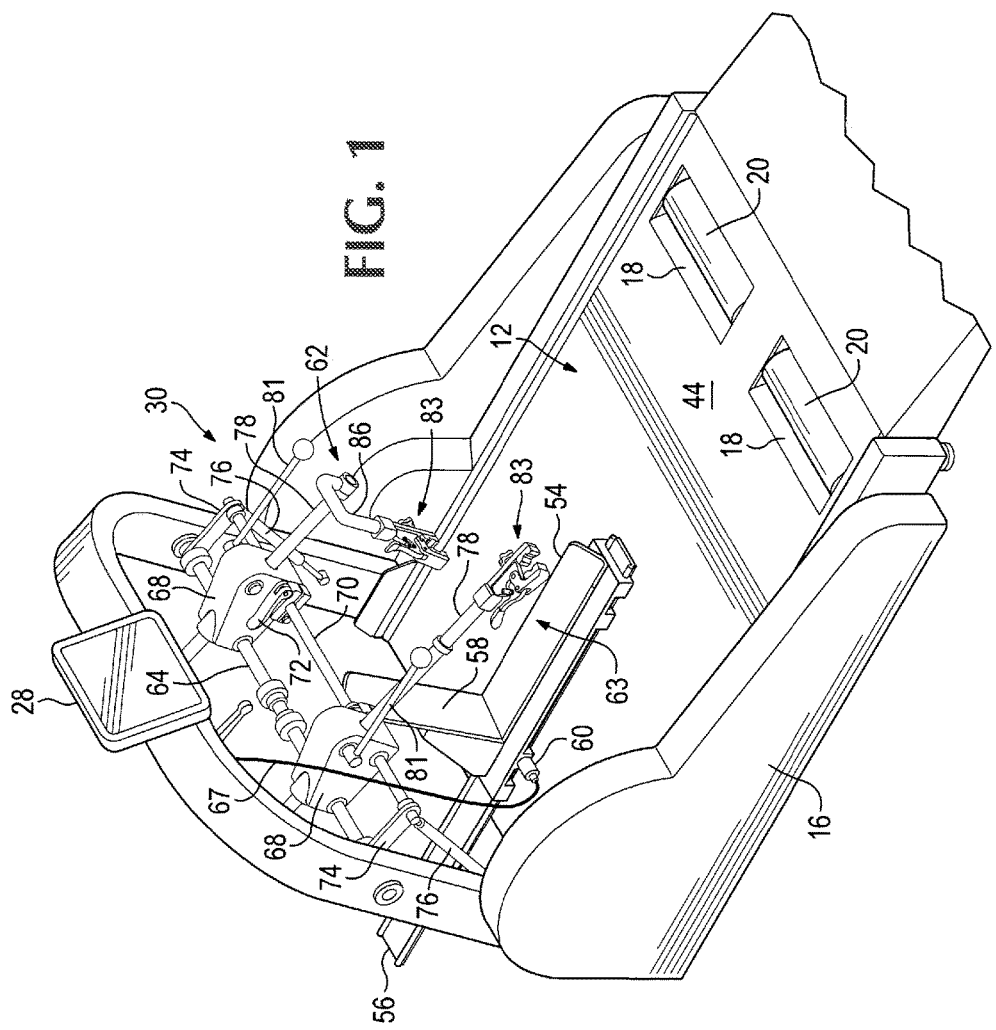
FIG. 1 is a perspective view showing a wheelchair exercise apparatus embodying the subject invention.
Figure 2:
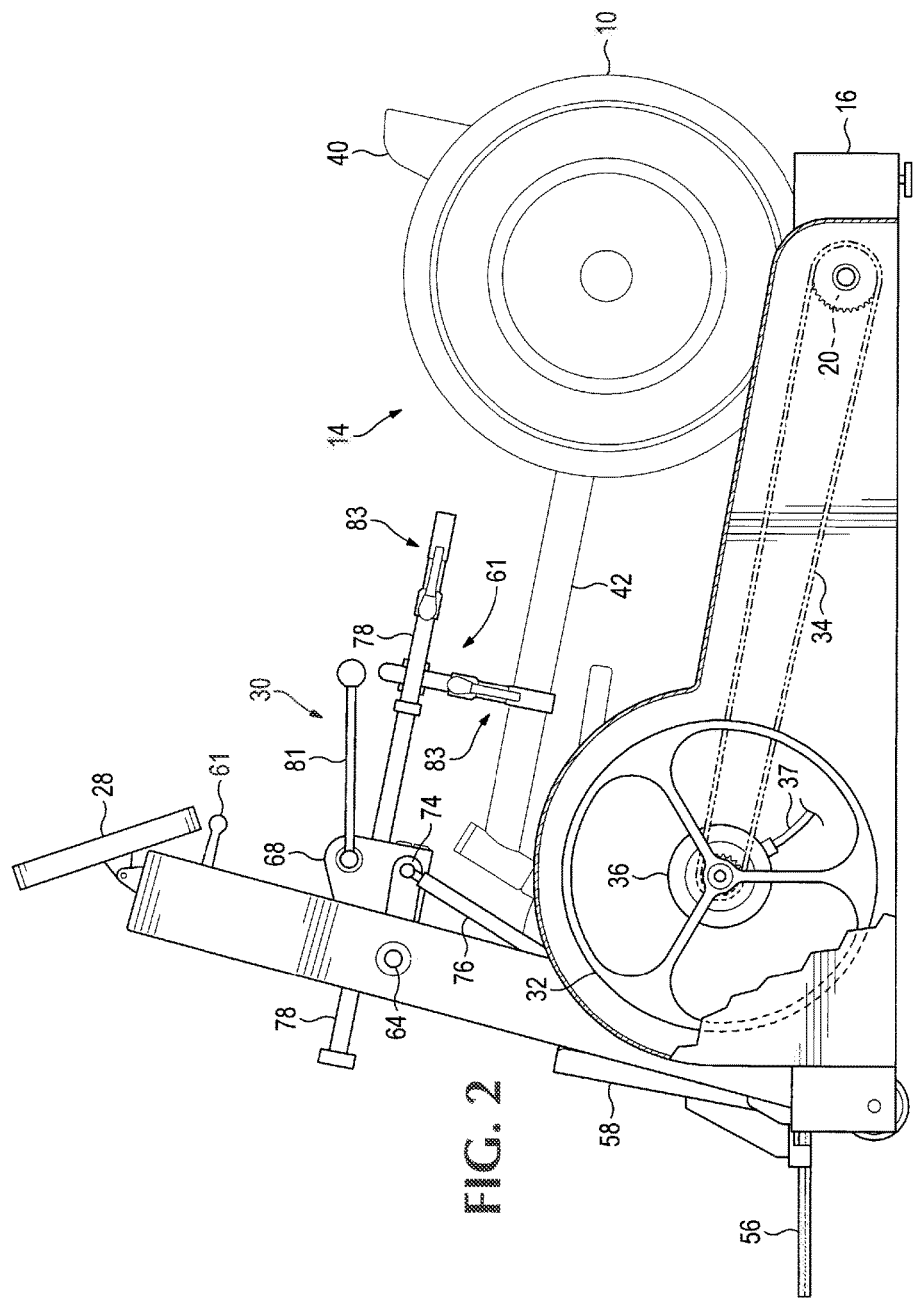
FIG. 2 is a side elevation view, partially cut away to show hidden detail.
Figure 3:
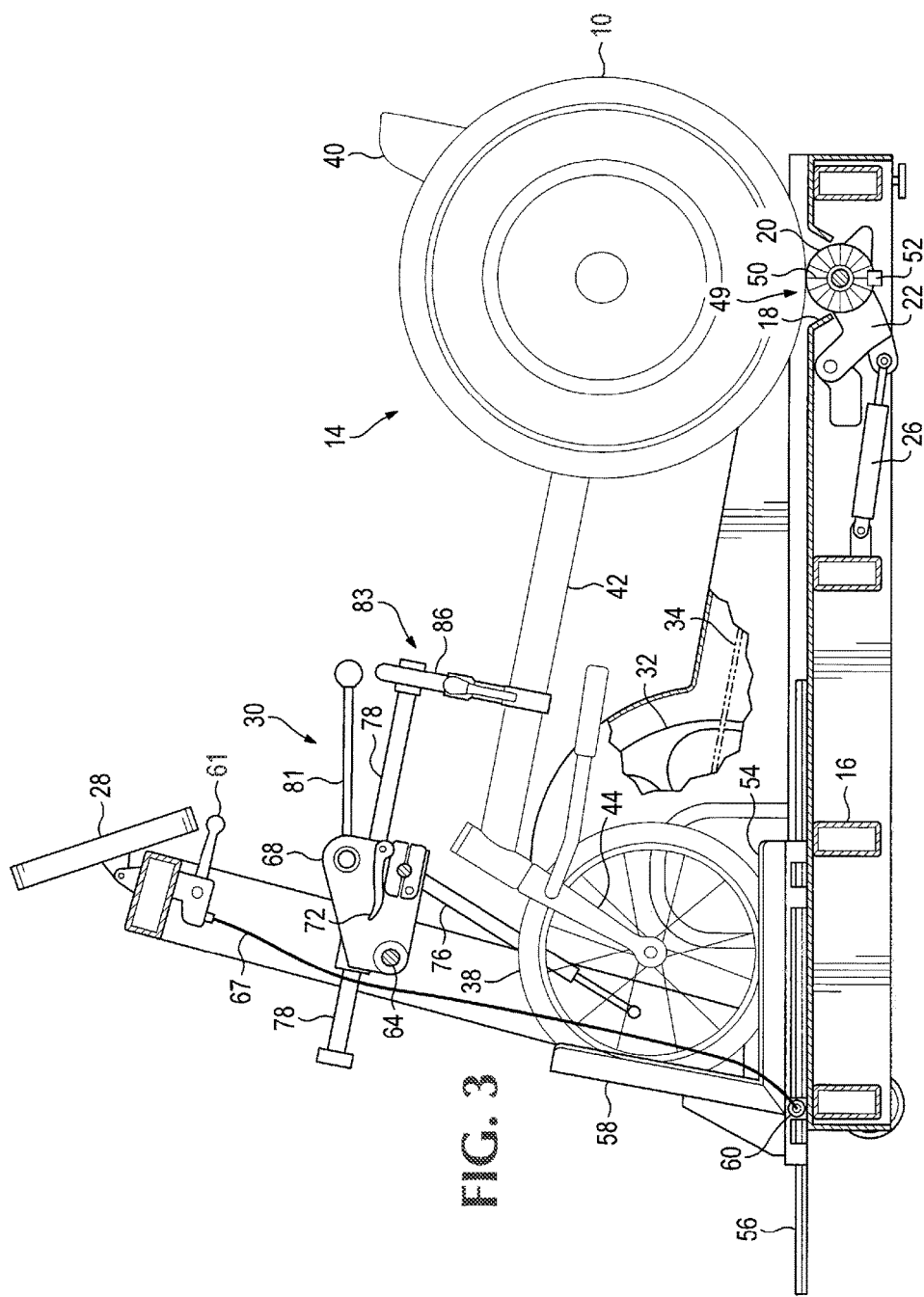
FIG. 3 is a side elevation view, partially cut away to show additional hidden detail.

Referring now to FIGS. 1-3 of the drawings, an exercise apparatus for wheelchairs having a pair of spaced apart side-by-side driving wheels 10 includes a platform 12, which a wheelchair 14 can be wheeled onto. The platform is supported above the surface the apparatus sits on by a frame 16, and is large enough to completely carry the wheelchair. Located near the end of the platform that the wheelchair is wheeled onto is a pair of elongated side-by-side slots 18 which extend transversely across the platform. The centers of the slots are separated from one another by approximately the same distance that the driving wheels are separated from one another. As a result when the wheelchair is driven onto the platform each driving wheel 10 is located over its own slots 18.

A pair of rollers 20 are rotatably mounted on the frame 16 such that the rollers rotate separately from one another, and one of the rollers 20 is centered in each slot 18. The rollers are carried by a lever 22, which is rotatably mounted on the frame 16 and allows the rollers 20 to simultaneously be moved between a lowered position, where they are below the top surface 24 of the platform, and a raised position, where they extend through the slots and their upper surfaces extend partially above the top surface of the platform. In the raised position the driving wheels 10 located above the slots are lifted off of the platform and are supported by the rollers. A piston cylinder 26 is used to move the rollers between their lowered and raised positions. In a preferred embodiment the piston cylinder is an electronically activated cylinder that is operated by conventional means through a monitor and control panel 28 located on the apparatus. Other types of piston cylinders could be used.

A clamping mechanism 30, which will be more fully described later, holds the wheelchair 14 immovably with respect to the apparatus when the driving wheels are centered over the slots and the rollers are in their raised position.

Referring now to FIGS. 2 and 3, each roller independently drives a flywheel 32. A chain or belt 34 is used for this in the embodiment shown in the drawings but conventional means such as direct coupling through gears could be used for this purpose. Each flywheel has a brake 36 which is configured to apply a variable amount of resistance to rotation of its associated flywheel. In a preferred embodiment the brake is a particle brake which is mounted on the frame 16 and has a rotatable output shaft that the flywheel is mounted on. The brake is controlled through control panel 28. A line 37 connects the brake with the control panel 28.

A speedometer system 49 measures the rotational speed of each roller, and thus the rotational speed of each driving wheel, independently. In the embodiment illustrated the speedometer system includes a series of equally spaced apart radial lines 50 located on the end of each roller. A sensor 52, mounted on the frame 16, is aligned longitudinally with the axis of the associated roller 20. The sensors are connected to the monitor/control panel 28 and are calibrated with the lines 50 in order to show the rotational speed of the roller. The control panel could include a computer programmed to convert the time it takes for adjacent lines to pass the sensor into the rotational speed of a driving wheel located on the roller, or the resulting speed of the wheelchair if it were located on the ground. The rotational speed of each driving wheel or the speed of the wheelchair is then displayed on the monitor.

While the subject exercise apparatus can be used with any wheelchair having a pair of side-by-side driving wheels, the embodiment shown in the drawings is unique in that it can be used with a sports wheelchair which has a single front wheel 38 that is located forwardly of the driving wheels 10 and is centered between the driving wheels. This type of sports wheelchair is shown in the drawings as having a seat 40, which is located generally between the driving wheels, and an elongate tubular frame 42 which extends between the driving wheels and a fork 44 which carries the third wheel

38. In order to accommodate a sports wheelchair the apparatus includes a U-shaped trough 54 which is located forward of and centered between the longitudinal centers of the rollers 20. The trough 54 is slidably mounted on a track 56 which is attached to the platform. Located at the end of the trough is an upstanding stop 58 which angles slightly forward as it extends upwardly from the trough. A latch 60, mounted on the trough 54, is movable between a locked position where it engages the track and holds the trough immovable relative to the track, and a released position where the trough is free to slide along the track. The latch 60 can be actuated mechanically by a lever 61 and cable 67, or electrically through a solenoid (not shown) which is actuated through the control panel 28. The latch 60 is actuated when the driving wheels are located over the slots 18 to prevent the wheelchair from moving further forward.

Figure 4:
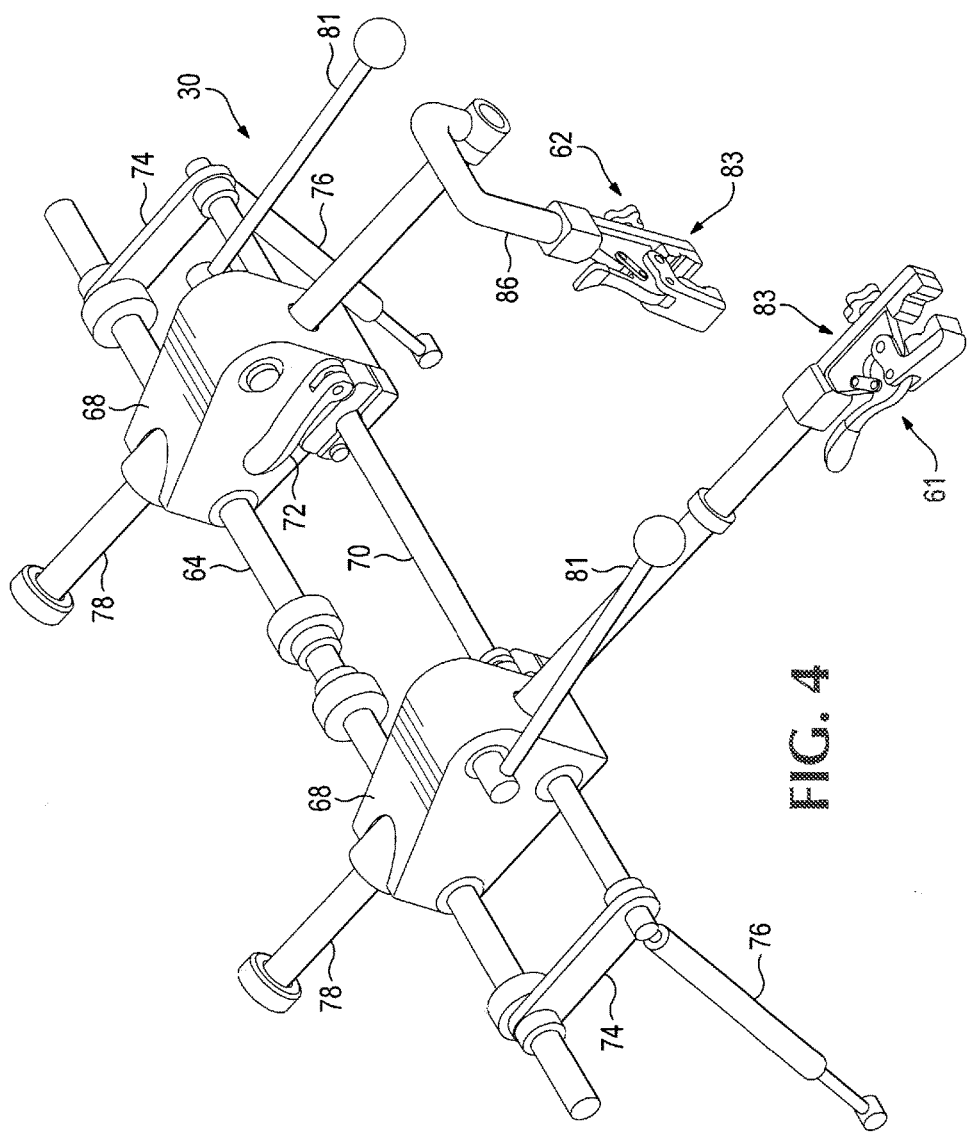
FIG. 4 is a perspective view of a lock mechanism that is part of the subject invention.
Figure 5:
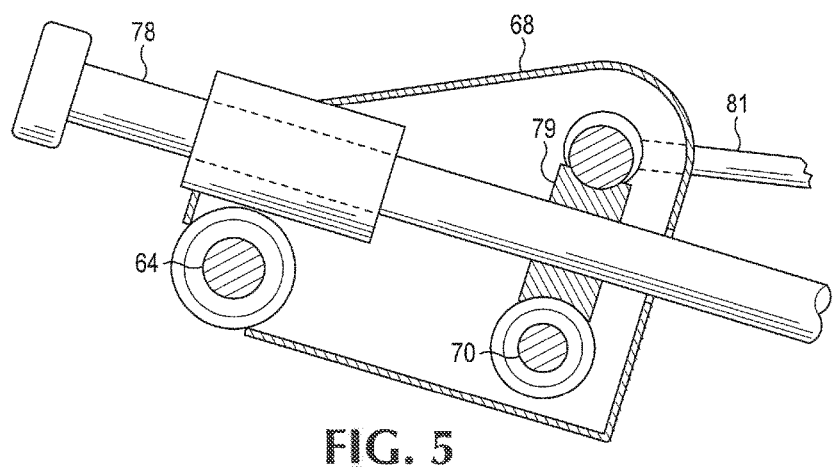
FIG. 5 is a cross-sectional view of a lock housing which is part of the locking mechanism.
Figure 6:
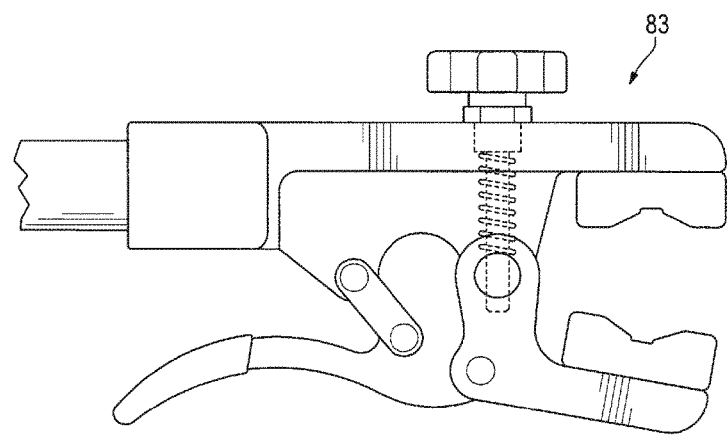
FIG. 6 is a detailed view of a clamp which is part of the locking mechanism.

Referring now also to FIGS. 4-6, a first clamping mechanism 63 is used for a regular wheelchair and a second clamping mechanism 62 is used for a three-wheel sports wheelchair. The clamping mechanisms are the same in most respects. They comprise a first mounting rod 64 which is rotatably mounted on the frame at each of its ends. A pair of lock housings 68 are slidably and rotatably mounted on the first mounting rod 64. A second mounting rod 70 extends slidably and rotatably through the lock housings 68 parallel with the first mounting rod 64. Clamps 72, located on each lock housing, lock the respective lock housing to the second mounting rod 70 when activated. Plates 74 connect the first and second rods rotatably at each end of the locking mechanism. An air cylinder 76 extends between each end of the second mounting rod and the frame. Thus the second mounting rod 70 can be rotated around the first mounting rod 64 when the clamps 72 are open, but the air cylinder 76 prevents the second mounting rod 70 from moving by itself. In addition the lock housings can be slid laterally along the mounting rods when the clamps 72 are open. An extension rod 78 extends slidably through each lock housing 68 perpendicular to the first and second mounting rods 64, 70. Clamps 79 are activated by levers 81 to clamp the extension rods to their respective lock housing. This adjustability allows the clamping mechanism to fit multiple sizes and shapes of wheelchairs. If the apparatus is being used with a regular wheelchair, a clamp 83 is mounted directly on both extension rods 78 which allows the clamp 83 to be attached to the wheelchair frame. If the apparatus is being used for a three wheel sports wheelchair the clamp 83 is mounted on a bent clamp arm 86 which is attached to one of the extension rods 78, which allows the clamp to be attached to the tubular frame 42 of the wheelchair.

In use, having individual rollers 20 and speedometer systems 79 for each driving wheel allows the user to determine which arm is the strongest so that more resistance can be added to the other driving wheel in order to strengthen the weaker arm. In addition, having individual rollers reach a driving wheel allows the driver to simulate making turns.

As noted previously, the resistance applied to each roller 20 is preferably capable of independent adjustment relative to the resistance applied to the other roller. One benefit of such a system is that a user may have an injury to one arm and may therefore want to relieve the resistance encountered by that arm relative to the other arm during the period of injury, while performing an exercise routine of the same or varying intensity over the period of exercise, and conversely may want to increase the resistance encountered by that arm to rehabilitate it after the injury has healed, for example. Similarly, when a person is recovering from a stroke, for example, rehabilitation may initially require limiting the resistance encountered by one arm relative to the other during an exercise routine with subsequent, gradual reductions in the difference in resistance applied to the patient's arms.

Figure 7:
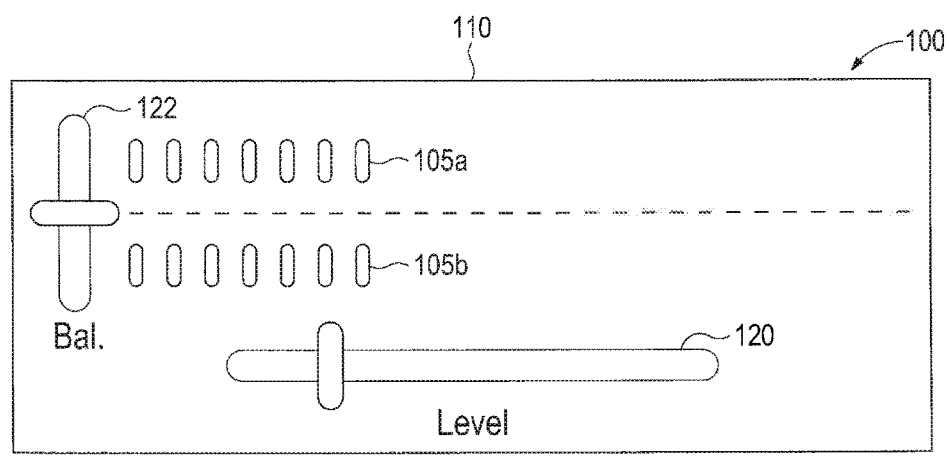
FIG. 7 is an exemplary control system for independently setting the respective resistances of brakes of a wheelchair exercise apparatus.

Referring to FIG. 7, an exemplary control system 100 is capable of determining the resistance applied to the roller 20 supporting the respective driving wheels 10 of a wheelchair supported on the disclosed exercise apparatus. The control system 100 preferably includes a display 110 by which the user may visualize the adjustments made by the control system 100 via, e.g. level indicator bars 105a and 105b, each representing the magnitude of the resistance applied to the left and right rollers respectively. A first level adjustment control 120 may be used to selectively increase or decrease the resistance of the rollers 20 in concert, i.e. to increase or decrease the intensity of the workout of the user. A second adjustment control 122 may be used to independently distribute the total resistance of the workout among the rollers 20. Thus, a user may shift more of the encountered resistance toward the left driving wheel than the right driving wheel, or vice versa, and do so independently of the total level of resistance applied to the rollers 20 via the level adjustment control 120.

Figure 8A:
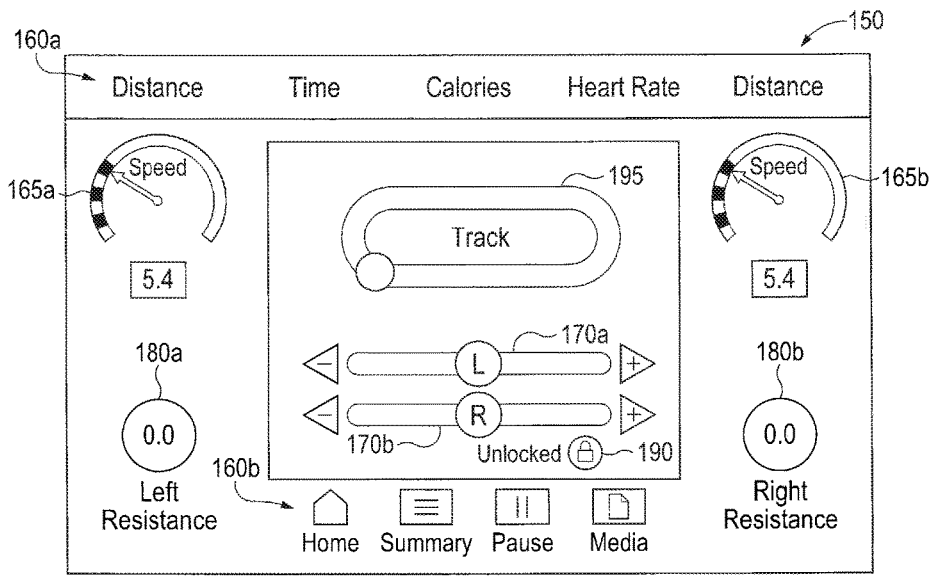
FIGS. 8A and 8B show alternate control system for independently setting the respective resistances of brakes of a wheelchair exercise apparatus.

FIG. 8A shows an alternate control system 150 capable of determining the resistance applied to the roller 20 supporting the respective driving wheels 10 of a wheelchair supported on the disclosed exercise apparatus. The control system 150 preferably includes a display by which the user may visualize the adjustments made by the control system 100, the speed of each driving wheel via left and right speedometers 165 *a* and 165 *b*, as well as various desired workout parameters 160 *a* e.g. distance traveled, heart rate, time elapsed, etc. The control system 150 may also preferably include a navigation panel 160 *b* by which a user may execute the functionality of the exercise apparatus to e.g. browse to a home screen to change the exercise routine, pause the exercise routine, access media such as music or television during the exercise routine, or display summary statistics about the exercise routine.

The control system 150 depicted in FIG. 8A also preferably indicates the resistance of each roller 120 relative to each other via adjustable resistance sliders 170a and 170b, and may also preferably indicate the numerical magnitude of the resistance for each of the rollers 20 via displays 180a and 180b.

Unlike the control system 100 of FIG. 7, in which the first level adjustment control 120 and the second level adjustment control 122 are implemented in separate interfaces, the control system 150 integrates the first and second level adjustment controls through a lock control 190 that alternately toggles the resistance sliders 170 *a* and 170b between a first mode in which an interface comprises resistance sliders 170 *a* and 170 *b* that may be moved independently to adjust the resistance of each in different increments, and an interface in which the resistance sliders 170 *a* and 170 *b* move in concert, i.e. any incremental adjustment of one slider will cause the same incremental adjustment in the other slider.

In some embodiments, the control system 150 (or 100) may visually indicate the current intensity of the exercise routine, which may or may not change over the duration of the routine. For example, in FIG. 8A, display 195 may show an exercise of constant intensity over the duration of the routine, represented by a display of a track, with a cursor or other indicator representing the current temporal location in that routine.

Figure 8B:
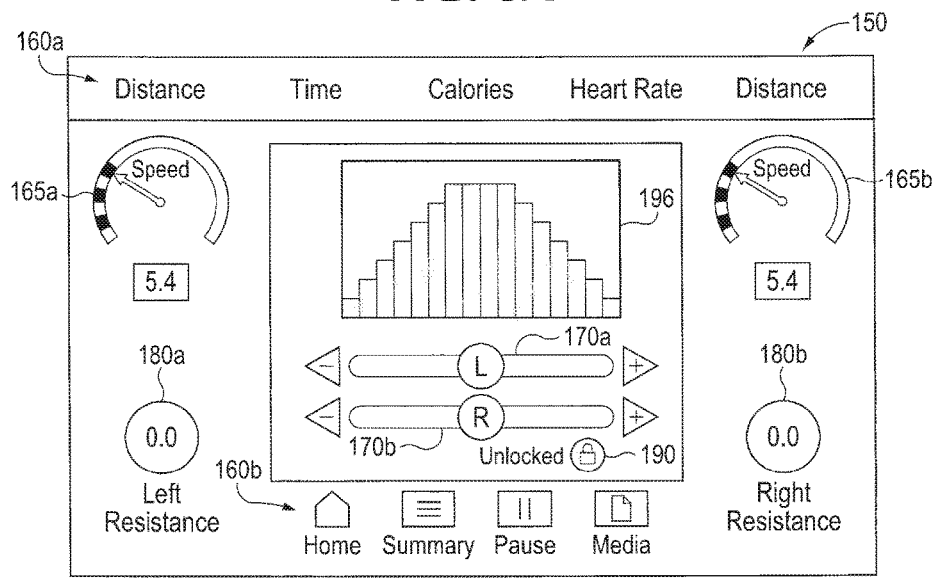

The exercise apparatus preferably includes a plurality of different exercise routines accessible through the control system 150 through, e.g. a "home" icon on panel 160b. FIG. 8B shows one such additional exercise routine, visually shown in display 196, which changes the intensity of the rollers over time. In this example, the disclosed exercise apparatus may automatically increment the magnitude of the resistance applied to each roller upwards and downwards, in tandem but according to any offset in resistance of the rollers relative to each other set by the user while the lock control 190 is set to the unlocked mode.

As noted earlier, the disclosed exercise apparatus is preferably capable of use for rehabilitative purposes, and specifically for instances in which one arm may be injured or otherwise incapable of the same level of performance as the other arm. Because of the variety of types and varieties of injuries, incapacities etc., the control system 150 is preferably capable of allowing a user to alternate between a number of different interfaces for modulating the resistances applied to the left and right rollers. For purposes of the specification and claims, an interface for modulating the resistance of the rollers refers to a graphical display allowing a user to interactively change the resistance applied to the rollers 20, and an interface is "different" from another if it allows a user a distinct functional control over the resistance of the rollers 20 not present in the other interface.

For example, as seen in FIGS. 9A and 9B, the panel 196 of the display 150 may optionally include a mode icon 200, depression of which causes the panel 196 to alternate between various interfaces for setting the resistances of the rollers 20. FIG. 9A shows a first such interface that allows a user to independently set the maximum resistance to be applied by each of the left and right rollers 20 via the sliders 170a and 170b. The exercise routine selected and displayed ion the panel 196 will then increment each of the left and right resistances according to the maximum values set. For example, in one embodiment, the exercise routine may simply use the maximum values to cap the resistance of one or more rollers below the level suggested in the display. In an alternate embodiment, the exercise routine may dynamically adjust the magnitude of the individual steps by which resistance is increased or decreased, using the maximum values set by the sliders 170a and 170, such that each of the rollers 170 is capable of being adjusted by the same number of increments, up to the selected maximum value. Those of ordinary skill in the art will appreciate that, rather than setting a maximum resistance, the sliders 170a and 170b may be used to set a minimum resistance such that the actual resistance applied to a roller 170a or 170b does not fall below the selected resistance, i.e. a floor, or may alternatively be used to adjust the increments by which resistance applied to a roller varies from the minimum set by the respective slider to the maximum permitted by the exercise apparatus.

FIG. 9B shows another alternate interface, again accessible through the mode icon 200, by which a user may use the sliders 170a and 170b to adjust both a minimum and maximum resistance independently for each of the rollers 20, using buttons 210a, 210b, 212a, and 212b. Again, in different embodiments (or different modes on the same exercise apparatus) the adjustments of the minimum and maximum values for each roller may either cap or clip the resistances at these levels or may dynamically adjust the magnitude of a fixed number of steps between the minimum and maximum levels. As seen in FIG. 9B, some embodiments may preferably also show a display that visually depicts the intensity of the resistance 214a of the left roller along with the intensity of the resistance 214b of the right roller simultaneously, even when those resistances are different. This may be achieved by any appropriate means, e.g. coloring, shading, cross-hatching, etc.

As seen in FIGS. 9A and 9B, these disclosed interfaces preferably also have a lock 190 as generally described earlier. Thus, with respect to the display shown in FIG. 9A, the lock 190 may be used to toggle the sliders 170a and 170b between a first mode where an interface moves the sliders in concert whenever any of the two are adjusted, and a second mode where an interface allows separate adjustment. The display shown in FIG. 9B may operate in the same fashion, or alternatively, the lock 90 may be used to toggle each individual slider between a first mode where an interface allows both the maximum and minimum values for a single slider to be moved independently, and a second mode where they move in concert. In still another embodiment, the lock 190 may toggle between three options: a first where the maximum and minimum resistances for both sliders move in concert when any resistance is adjusted; a second where maximum and minimum resistances for a single sliders move in concert when either the maximum or minimum resistance of that slider is adjusted, and a third where each of the maximum and minimum resistance of each slider is adjustable independently of any other resistance.

In some embodiments, changes in intensity of the rollers may be implemented by voice activation. This is particularly useful in a wheelchair exercise apparatus where a user may not wish to remove a hand from a wheel, interrupting exercise, to effect an adjustment of the resistance of a roller. For example, the control system 150 may be programmed to recognize a variety of voice commands to adjust resistances of rollers independently, or in concert as desired by e.g. using a first command to toggle a mode, a second command to select a slider, and a third command to adjust the slider, etc. Alternatively, the control system 150 may be programmed to adjust the difference between resistances of rollers in incremental steps via voice commands.

The terms and expressions that have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims that follow.

The invention claimed is:

1. An exercise apparatus for a wheelchair having a pair of side-by-side driving wheels, said apparatus comprising:
    (a) a platform having an upper surface configured to support said wheelchair;
    (b) first and second elongate rollers rotatably mounted on said platform and located on said platform such that one of said driving wheels is supported above said platform by one of said first and second elongate rollers and the other of said driving wheels is supported above said platform by the other of said first and second elongate rollers when said wheelchair is on said platform;
    (c) first and second brakes, each associated with a respective one of said first and second elongate rollers, wherein each of said first brake and said second brake is configured to apply a variable resistance to its respectively associated elongate roller having a magnitude independent of that applied by the other one of said first brake and said second brake; and
    (d) a graphical display control system including an intensity control configured to modulate a total resistance that is provided by a combination of the variable resistances of the first and second brakes and that is distributively applied to the first and second elongate rollers and a balance control configured to modulate a distribution of the total resistance that is distributively applied to the first and second elongate rollers, wherein the intensity control selectively increases or decreases the total resistance that is provided by the combination of the variable resistances of the first and second brakes that is distributed according to the balance control.

2. The exercise apparatus of claim 1, wherein the intensity control and the balance control are displayed simultaneously with one another in the graphical display control system.

3. The exercise apparatus of claim 2, wherein the graphical display control system additionally includes a mode control that selectively alternates the graphical display control system between a first mode and a second mode.

4. The exercise apparatus of claim 1, wherein the exercise apparatus is programmed to implement an exercise routine that automatically changes the total resistance that is provided by the combination of the variable resistances of the first and second elongate rollers using a setting of the balance control.

5. A method of setting a resistance applied to driving wheels of a wheelchair mounted on an exercise apparatus, the method comprising:

using a first control of the exercise apparatus to modulate a resistance applied to a first elongate roller and a second elongate roller of the exercise apparatus, the first and second elongate rollers being rotatably mounted on a platform of the exercise apparatus and that are located on the platform such that a first driving wheel of the wheelchair is supported above the platform by the first elongate roller and such that a second driving wheel of the wheelchair is supported above the platform by the second elongate roller; and using a second control of the exercise apparatus to alternate between different interfaces of the exercise apparatus, wherein each interface of the different interfaces includes the first control, and wherein the first control modulates the resistance applied to the first and second elongate rollers.

\* \* \* \* \*